(12) United States Patent
Nordstrom et al.

(10) Patent No.: US 9,308,365 B2
(45) Date of Patent: Apr. 12, 2016

(54) DETACHABLE ELECTRODE AND ANCHOR

(71) Applicant: BIOTRONIK SE & Co. KG, Berlin (DE)

(72) Inventors: Karl Nordstrom, Woodburn, OR (US); Michael J. Ayton, Beaverton, OR (US); Matthias Wenzel, Berlin (DE)

(73) Assignee: BIOTRONIK SE & CO. KG, Berlin (DE)

( * ) Notice: Subject to any disclaimer, the term of this patent is extended or adjusted under 35 U.S.C. 154(b) by 6 days.

(21) Appl. No.: 14/037,273

(22) Filed: Sep. 25, 2013

(65) Prior Publication Data

US 2014/0148675 A1 May 29, 2014

Related U.S. Application Data

(60) Provisional application No. 61/730,064, filed on Nov. 27, 2012.

(51) Int. Cl.
| | | |
|---|---|---|
| *A61B 5/042* | (2006.01) | |
| *A61N 1/05* | (2006.01) | |
| *A61N 1/375* | (2006.01) | |
| *A61N 1/362* | (2006.01) | |

(52) U.S. Cl.
CPC ............... *A61N 1/059* (2013.01); *A61B 5/042* (2013.01); *A61N 1/057* (2013.01); *A61N 1/362* (2013.01); *A61N 1/375* (2013.01)

(58) Field of Classification Search
CPC ...... A61B 5/042; A61B 5/0422; A61N 1/057; A61N 2001/0578

USPC .......................... 600/374, 375; 607/126–128
See application file for complete search history.

(56) References Cited

U.S. PATENT DOCUMENTS

| | | | |
|---|---|---|---|
| 5,383,924 A | | 1/1995 | Brehier |
| 5,807,399 A | * | 9/1998 | Laske et al. ................... 607/126 |
| 6,188,932 B1 | | 2/2001 | Lindegren |
| 6,459,937 B1 | | 10/2002 | Morgan et al. |
| 9,020,611 B2 | * | 4/2015 | Khairkhahan et al. ........ 607/127 |
| 2007/0043414 A1 | * | 2/2007 | Fifer et al. .................... 607/126 |
| 2011/0251661 A1 | | 10/2011 | Fifer et al. |

FOREIGN PATENT DOCUMENTS

EP        0041254        * 12/1981

OTHER PUBLICATIONS

European Search Report, dated Jan. 8, 2014, 6 pages.

* cited by examiner

*Primary Examiner* — Lee S Cohen
(74) *Attorney, Agent, or Firm* — ARC IP Law, PC; Joseph J. Mayo

(57) ABSTRACT

A detachable electrode and anchor utilized with electrode leads and leadless medical implants that enable explantation of the electrode while leaving the anchor in place. The detachable electrode and anchor utilizes a detachable mechanism that detachably couples the electrode to the anchor. Embodiments do not require removal of existing scar tissue before explantation, which minimize chances of internal bleeding at the extraction site. Embodiments also minimize impact on the vein in which the electrode lead travels by eliminating use of a necessarily larger diameter sheath that is utilized around the electrode lead to remove the electrode lead and attached anchor.

13 Claims, 5 Drawing Sheets

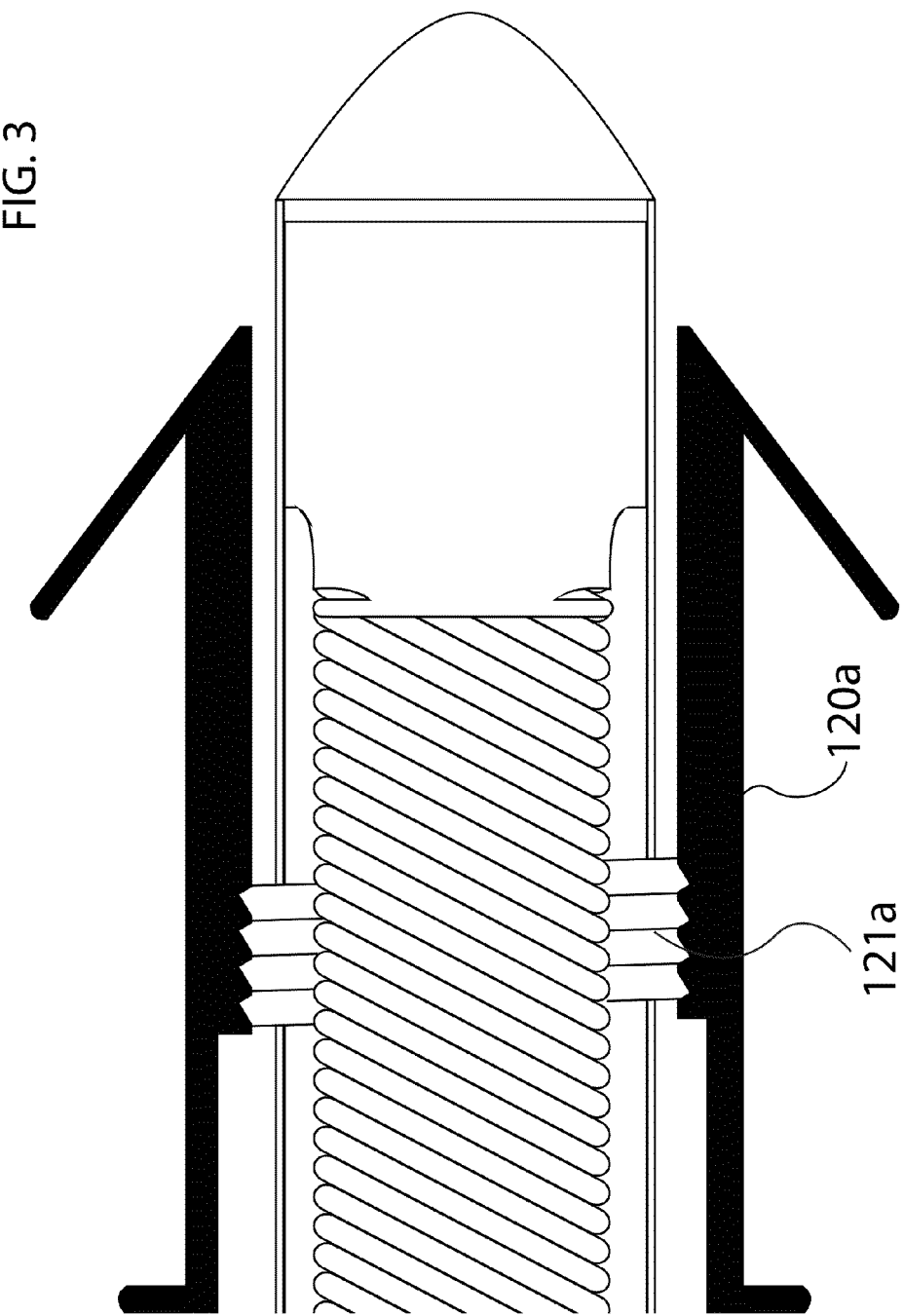

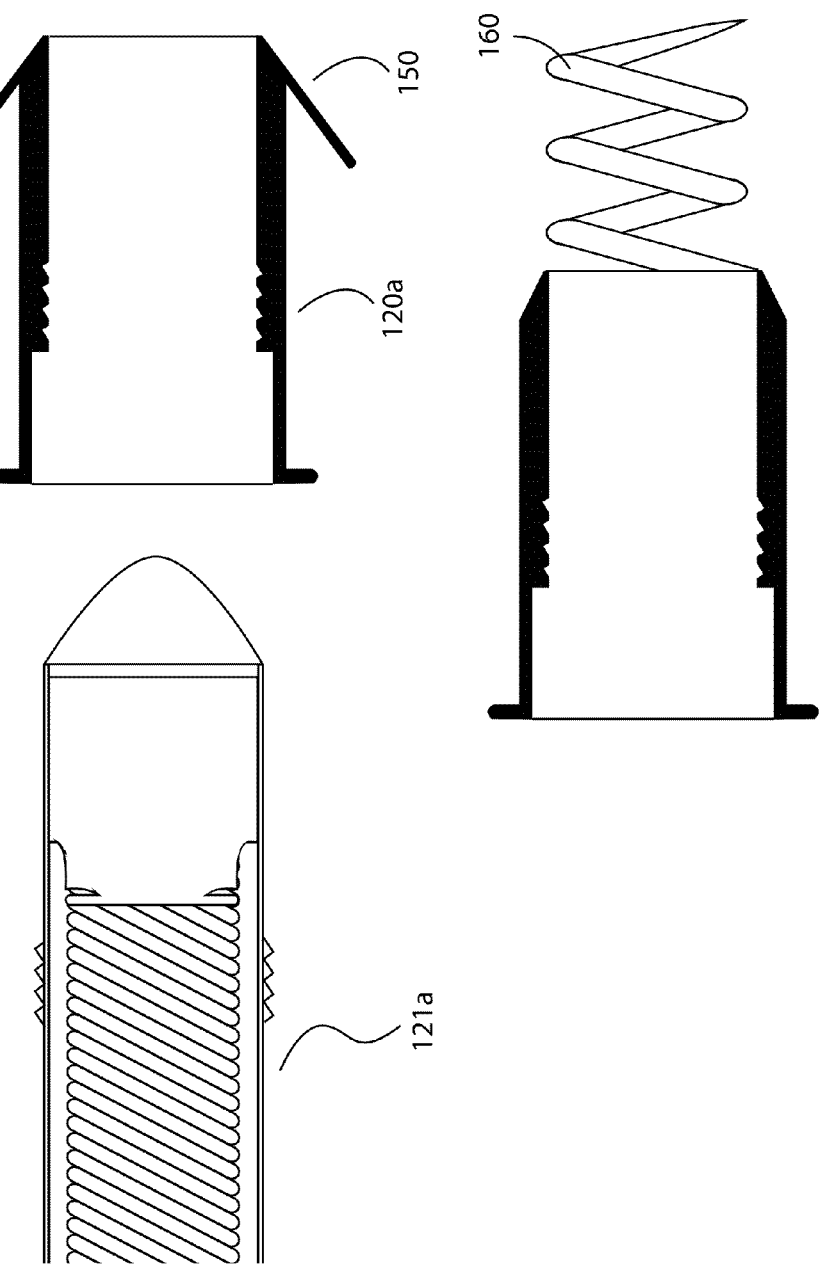

DETACHABLE ELECTRODE AND ANCHOR

This application claims the benefit of U.S. Provisional Patent Application 61/730,064, filed on 27 Nov. 2012, the specification of which is hereby incorporated herein by reference.

BACKGROUND OF THE INVENTION

1. Field of the Invention

At least one embodiment of the invention generally relates to implantable medical devices that may later be detached and which may include electrodes, including electrode leads and leadless medical implants having at least one electrode and more particularly, but not by way of limitation, embodiments of the invention relate to a detachable electrode and anchor that may be detachably released from one another to explant the electrode and associated lead or leadless implant.

2. Description of the Related Art

Electrodes in the form of electrode leads or leadless medical implants are commonly implanted in patients in need of cardiac monitoring and if necessary, electrical stimulation. Electrical energy is sensed over the electrodes and analyzed, generally with an associated implantable medical device, or external device. Therapeutic energy is provided to the electrodes implanted in a heart for example to ensure that the heart provides life-sustaining contractions that pump blood through the patient's body. Generally, electrodes are physically attached to the heart in a manner that is intended to be relatively permanent, so as to ensure long term robust electrical contact with the specific heart tissue that the electrode is attached to. Typical electrodes provide attachment mechanisms such as screws or tines that project in one way or another into the tissue of the heart. Leadless devices have many advantages includes avoiding problems associated with lead failure.

When an electrode lead is no longer needed, or becomes inoperable, or otherwise is to be replaced, the electrode lead may be left in place, or removed. Leaving unused electrode leads in place is suboptimal in that the unused leads may interfere with the internal workings of the veins or portion of the heart in which they remain. Alternatively, removing the electrode lead may damage the tissue where the electrode lead is attached. If the electrode lead is to be removed, one such method of removing an unwanted electrode lead requires use of an additional sheath that is placed over the electrode lead that abuts against the heart tissue where the electrode lead is attached. The electrode lead is then physically removed from the scar tissue that has grown around the attachment portion or anchor of the electrode lead, for example the tines. Optionally, a laser or mechanical drill may be utilized to cut or otherwise remove scar tissue surrounding the tines before the anchor of the electrode lead is removed. The main problem with this technique is that the extraction site is subject to internal bleeding. Leadless medical implants on the other hand are generally never removed and remain attached to tissue even after a battery within the device is drained, which is also suboptimal.

BRIEF SUMMARY OF THE INVENTION

At least one embodiment of the invention provides a detachable electrode and anchor that enables explantation of the electrode lead or leadless implantable device while leaving the anchor in place. In one or more embodiments, the electrode may include a tip electrode, an insulating electrode body and at least one electrically conductive wire internally situated within an electrode lead embodiment, and having a first detachable element. The anchor generally includes at least one projection configured to physically attach the anchor to tissue, for example heart tissue, and a second detachable element. Embodiments of the invention may enable the first detachable element to detachably engage the second detachable element to enable the anchor to remain implanted and enable the electrode to be explanted, when the electrode is removed or replaced for example. The electrode generally includes at least one conductive outer surface area and insulative portions therebetween. Any type of material may be utilized for the conductive and insulative areas that are generally biocompatible, as one skilled in the art will appreciate. The anchor may be constructed from any material, of any hardness or flexibility depending on the intended application. Embodiments do not require removal of existing scar tissue before explantation, which minimize chances of internal bleeding at the extraction site. Embodiments also minimize impact on the vein in which the electrode travels by eliminating use of a necessarily larger diameter sheath that is utilized around the electrode to remove the electrode and attached anchor for example.

The first detachable element associated with the electrode may include at least one radially outward oriented projection that is for example radially retracted, when the electrical conductor is elongated through a rearward force imposed at the proximal end of the electrical conductor. By stretching or otherwise elongating the electrical conductor, the inner pitch of the electrical conductor increases, which reduces the outer diameter of the electrical conductor, which reduces the force against at least one radially outward oriented indentation, and for example disengages at least one projection from at least one indentation. Alternatively, in one or more embodiments the indentation is inwardly oriented into the electrical conductor and the projection is inward from the anchor towards the centerline of the apparatus that is defined as the innermost portion of the cylindrical electrode line parallel to the direction of the electrode body for example. In this embodiment, the first detachable element associated with the electrode includes at least one radially inward oriented indentation.

Embodiments of the first detachable element associated with the electrode may include at least one bearing, wherein the second detachable element in the anchor includes an indentation that may engage the at least one bearing. Alternatively, the first detachable element associated with the electrode includes an indentation, wherein the second detachable element in the anchor includes at least one bearing that may engage the indentation.

The embodiments that employ bearings may couple with a ring type indentation, in which case the coupling is an axial rotational coupling or multiple indentations for example that correspond to more or less of the bearings to facilitate fixed rotational relationship between the electrode and anchor. Embodiments may also employ a ring projection to enable a rotational type coupling between the electrode and anchor. For example, in one or more embodiments, the first detachable element includes a ring for example that projects outwardly and wherein the second detachable element in the anchor includes an indentation wherein the indentation may engage the ring. Alternatively, the first detachable element includes at least one radially inward oriented indentation, wherein the second detachable element in the anchor includes a ring that may engage the at least one radially inward oriented indentation.

In one or more embodiments, the first detachable element includes a temperature dependent hardness. Example temperature dependent hardness characteristics include shape memory, superelasticity and any other physical characteristic that may be changed over a biocompatible temperature range. An example material that exhibits this type of physical property includes nickel titanium, otherwise known as nitinol. Any other material that may change shape based on temperature may be utilized in keeping with the spirit of the invention. For example, by cooling the detachable elements, they may deform, become superelastic, more flexible or otherwise more able to detach. The temperature change may be asserted in the form of cooling the anchor or distal end of the electrode, either from within the lead by injecting cool or cold biocompatible liquids having a biocompatible temperature, or by externally cooling the area around the anchor or electrode. For types of materials that change physical properties when heated, heated liquids or heating elements may be utilized to lower the disengagement force between the detachable elements. Any temperature dependent change that lowers the force required to disengage the detachable elements and any material that includes biocompatible temperature dependent hardness may be utilized for embodiments of the detachable elements in keeping with the spirit of the invention. The temperature dependent material may also be utilized for the second detachable element as well, or for both the first and second detachable elements.

The first detachable element may include a first threaded element and the second detachable element in the anchor may include a second threaded element configured to rotationally engage the first threaded element. This embodiment allows for rotational forces near the end of the electrode to disengage the electrode from the anchor. The attachment mechanism on the anchor may also include or otherwise employ a helix, for example of the opposing rotational orientation with respect to the threads, so that rotation in one clockwise direction to detach the detachable elements from one another does not disengage the helix from the tissue, but rather provides a force associated with insertion of the helix.

BRIEF DESCRIPTION OF THE DRAWINGS

The above and other aspects, features and advantages of at least one embodiment of the invention will be more apparent from the following more particular description thereof, presented in conjunction with the following drawings wherein:

FIG. 3 shows a side view of a second embodiment of the invention in the attached state.

FIG. 4 shows a side view of a second embodiment of the invention in the detached state.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
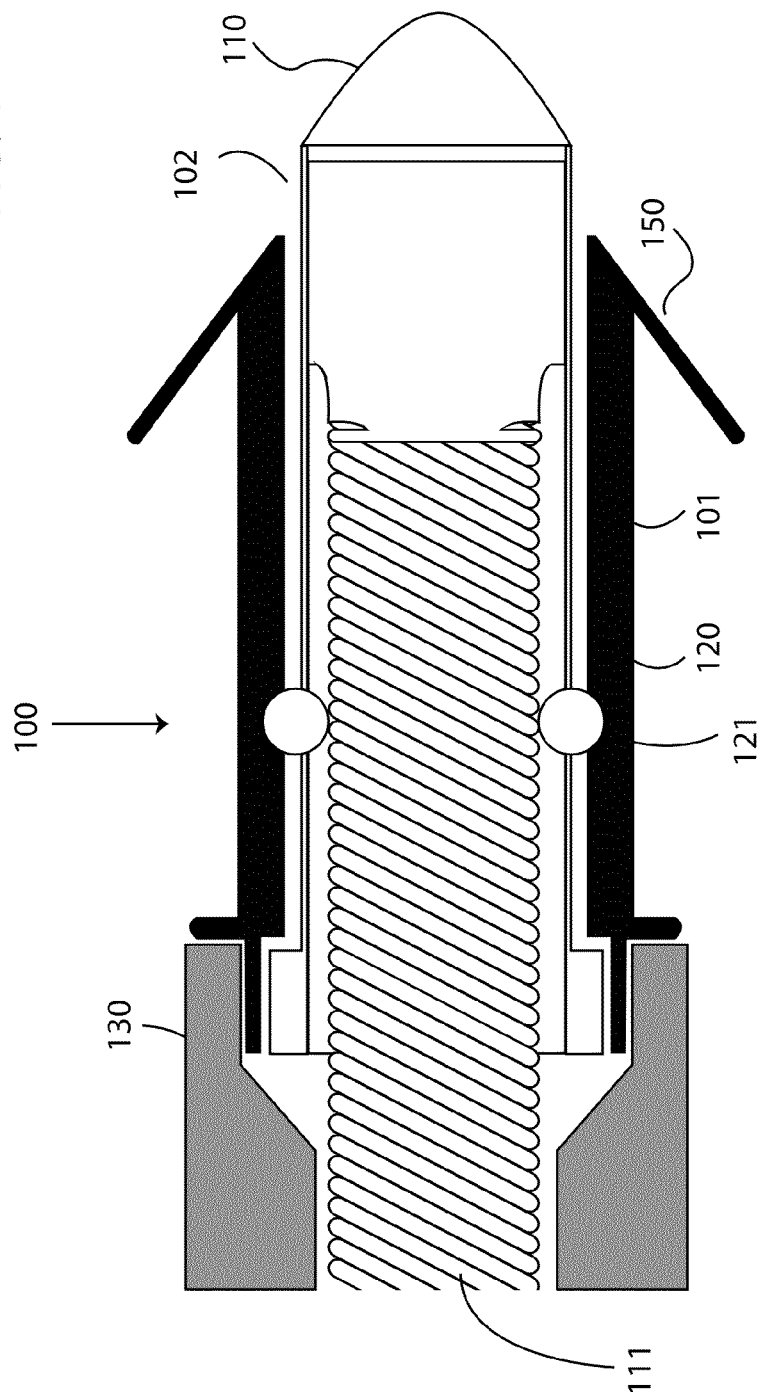
FIG. 1 shows a side view of a first embodiment of the invention in the attached state.
Figure 1A:
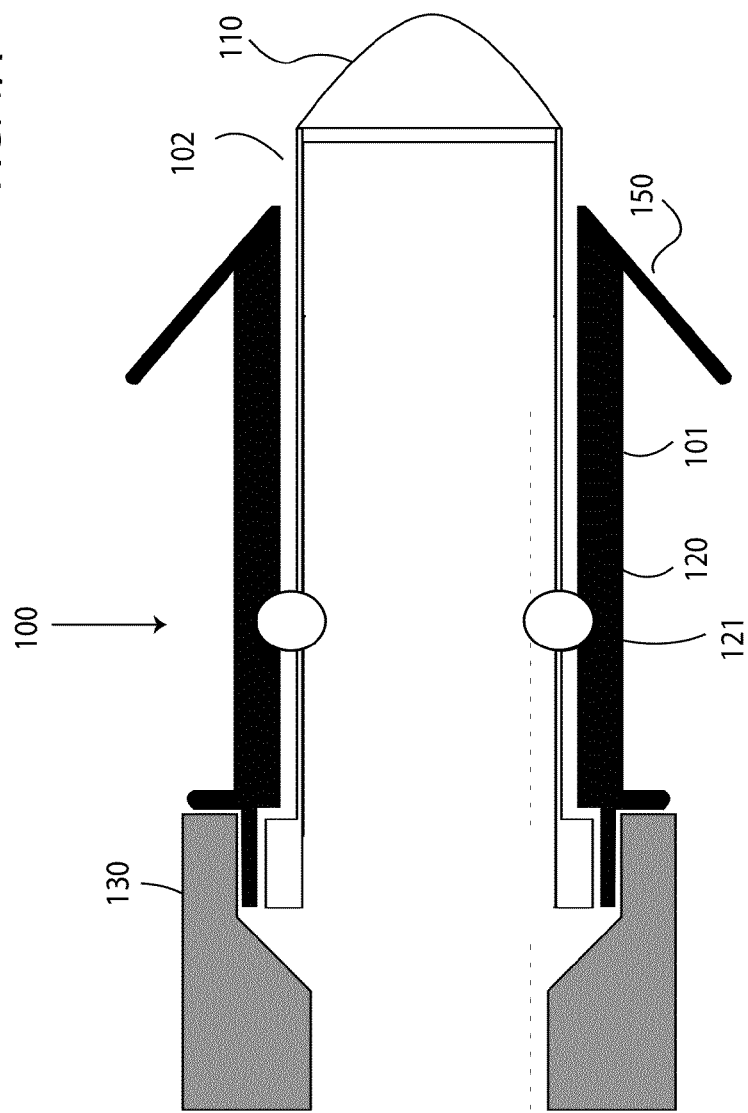
FIG. 1A shows a side view of an electrode device as a leadless device.

FIG. 1 shows a side view of a first embodiment of the invention in the attached state that includes anchor 101 and a detachable electrode 102, which may be an electrode lead or a leadless medical implant. FIG. 1A shows a side view of the electrode device as a leadless device. The electrode lead is shown in FIG. 1 as a coiled wire, while the leadless device is shown in FIG. 1A and excludes the coiled wire for example. All examples given with respect to an electrode lead may be applied equally to a leadless medical implant, such as a leadless pacemaker, drug reservoir, drug pump or any other type of leadless medical implant. Although many examples are given with respect to electrode leads, this does not limit the use of the apparatus described herein to electrode leads, but is described with respect to electrode leads for brevity.

In one or more embodiments, the electrode lead embodiment includes an electrode, such as tip electrode 110, insulating electrode body 130 and at least one electrically conductive wire 111 internally situated within the electrode lead and having a first detachable element 121. Leadless devices do not require wire 111 and communicate with wireless electromagnetic waves generally.

Anchor 101 generally includes at least one projection 150 configured to physically attach the anchor to tissue, for example heart tissue, and a second detachable element 120. Embodiments of the invention enable the first detachable element to detachably engage the second detachable element to enable the anchor to remain implanted and enable the electrode to be explanted, when the electrode is removed or replaced for example. The electrode lead generally includes at least one conductive outer surface area and insulative portions therebetween. Any type of material may be utilized for the conductive and insulative areas that are generally biocompatible, as one skilled in the art will appreciate. The anchor may be constructed from any material, of any hardness or flexibility depending on the intended application.

Figure 2:
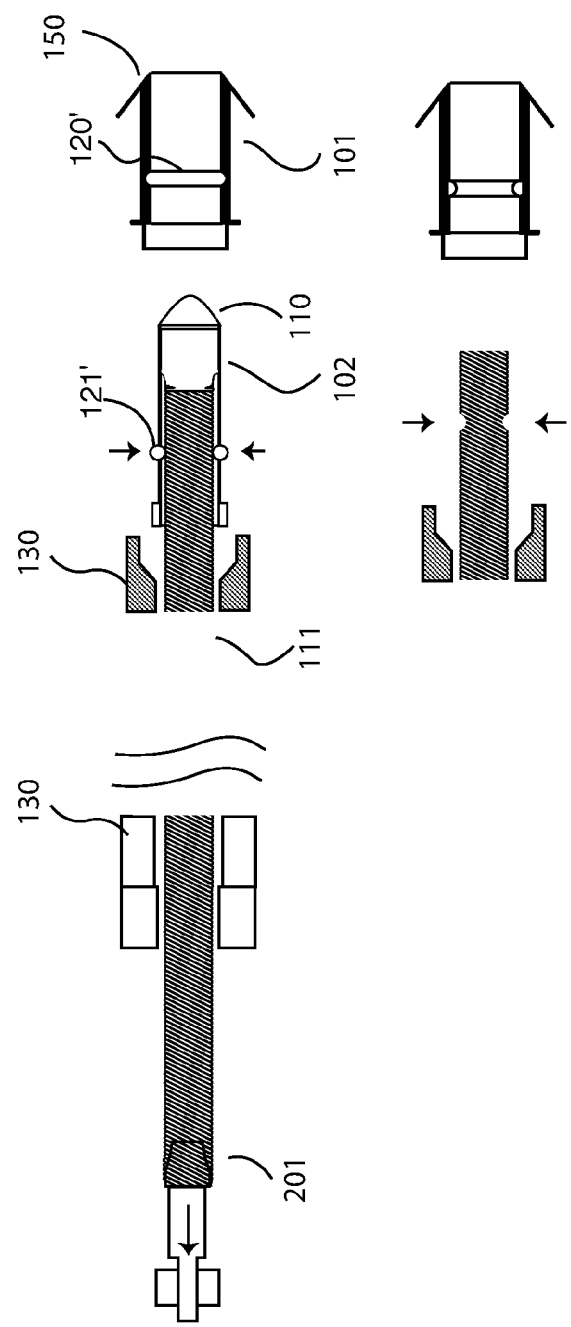
FIG. 2 shows a side view of a first embodiment of the invention in the detached state.

FIG. 2 shows a side view of a first embodiment of the lead based apparatus in the detached state. As shown, the first detachable element in the electrode lead may include at least one radially outward oriented projection 121' that is for example radially retracted, when electrical conductor 111 is elongated through a rearward force imposed at the proximal end 201 of electrical conductor 111. By stretching or otherwise elongating the electrical conductor 111, the inner pitch of the electrical conductor increases, which reduces the outer diameter of the electrical conductor, which reduces the force against the at least one radially outward oriented indentation 120', and for example disengages projection 121' from indentation 120'. In the case of leadless implantable devices, the sides of the leadless device may also be non-rigid, and which elongate, and thus narrow when a longitudinal force is applied.

Alternatively, as shown in the bottom portion of the figure, in one or more embodiments the indentation is inwardly oriented into the electrical conductor and the projection is inward from the anchor towards the centerline of the apparatus that is defined as the innermost portion of the cylindrical electrode line parallel to the direction of the electrode body for example. In this embodiment, the first detachable element in the electrode lead includes at least one radially inward oriented indentation, e.g., element 121' is part of the anchor while the indentation 120' is part of the electrode lead. Leadless devices may also include a corresponding indentation.

Embodiments of the first detachable element associated with the electrode may include at least one bearing, wherein the second detachable element in the anchor includes an indentation that may engage the at least one bearing. Alternatively, the first detachable element in the electrode lead includes an indentation, wherein the second detachable element in the anchor includes at least one bearing that may engage the indentation.

The embodiments that employ bearings may couple with a ring type indentation, in which case the coupling is an axial rotational coupling or multiple indentations for example that correspond to more or less of the bearings to facilitate fixed rotational relationship between the electrode lead and anchor.

Embodiments may also employ a ring projection to enable a rotational type coupling between the electrode lead and anchor. For example, in one or more embodiments, the first detachable element in the electrode lead includes a ring for example that projects outwardly and wherein the second detachable element in the anchor includes an indentation wherein the indentation may engage the ring. Alternatively, the first detachable element in the electrode lead includes at least one radially inward oriented indentation, wherein the second detachable element in the anchor includes a ring may engage the at least one radially inward oriented indentation.

In one or more embodiments, the electrode lead is flexible, and requires force to reduce the diameter of the electrode lead. In this embodiment, the first detachable element and the second detachable element are coupled together based on radially outward force provided by the electrode lead. As described above, when the end of the electrode lead is extended away from the anchor, the pitch of the electrical conductor is increased, which decreases the diameter of the electrode lead, reduces the force between the electrode lead and anchor to the point at which the electrode lead may be removed from the anchor without explanting the anchor. Hence as long as the force required to detach the electrode lead from the anchor is less than the force required to explant the anchor from the tissue, then the detachable elements are acceptable according to embodiments of, and in keeping with the spirit of the invention. The same technique may be utilized with flexible embodiments of leadless devices, or leadless devices that are rigid and include a compressible ring or bearings as one skilled in the art will recognize. A wire with a hook or any other device may be utilized to exert a longitudinal force to the leadless implant as desired in any manner that is capable of supplying a longitudinal force to the implant. Alternatively, the first detachable element and the second detachable element may be coupled together at least based on radially inward force provided by the anchor. For example, in embodiments that employ a flexible anchor, the anchor may squeeze or in any other manner impart force on the detachable element in the electrode lead. In one or more embodiments, the first detachable element and the second detachable element are coupled together based on radially outward force provided by the electrode lead and radially inward force provided by the anchor. One skilled in the art will appreciate that in a static orientation, force applied from one detachable element is opposed by the corresponding detachable element in the other object, otherwise motion occurs. By force as described herein, it is the primary supplier of force that is described, not the opposing force element.

In one or more embodiments, the first detachable element includes a temperature dependent hardness. Example temperature dependent hardness characteristics include shape memory, superelasticity and any other physical characteristic that may be changed over a biocompatible temperature range. An example material that exhibits this type of physical property includes nickel titanium, otherwise known as nitinol. Any other material that may change shape based on temperature may be utilized in keeping with the spirit of the invention. For example, by cooling the detachable elements, they may deform, become superelastic, more flexible or otherwise more able to detach. The temperature change may be asserted in the form of cooling the anchor or distal end of the electrode lead, either from within the lead by injecting cool or cold biocompatible liquids having a biocompatible temperature, or by externally cooling the area around the anchor or electrode lead. For types of materials that change physical properties when heated, heated liquids or heating elements may be utilized to lower the disengagement force between the detachable elements. Any temperature dependent change that lowers the force required to disengage the detachable elements and any material that includes biocompatible temperature dependent hardness may be utilized for embodiments of the detachable elements in keeping with the spirit of the invention. The temperature dependent material may also be utilized for the second detachable element as well, or for both the first and second detachable elements. The same mechanisms described with respect to electrode lead embodiments may be applied to leadless implantable devices as well.

FIG. 3 shows a side view of a second embodiment of the invention in the attached state. In this embodiment, the first detachable element in the electrode lead may include a first threaded element 121a and the second detachable element 120a in the anchor may include a second threaded element capable of rotationally engaging the first threaded element. This embodiment allows for rotational forces at the end of the electrode lead to disengage the electrode lead from the anchor. Leadless devices may also include hex nuts or facets in any number or spanner type coupling elements or slots or any other geometric shape that allows for rotational forces to be applied to couple the leadless device to the anchor as one skilled in the art will recognize.

FIG. 4 shows a side view of a second embodiment of the invention in the detached state. Although the attachment mechanism 150 is shown as rearward oriented tines, the attachment mechanism may also include a helix 160, for example of the opposing rotational orientation with respect to the threads 120a and 121a, so that rotation in one clockwise direction to detach the detachable elements from one another does not disengage the helix from the tissue.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A detachable electrode and anchor comprising:
   a leadless medical implant comprising
      a first detachable element, and,
      an electrode comprising at least one electrically conductive element, wherein said electrode is coupled with said first detachable element;
   an anchor comprising at least one projection configured to physically attach said anchor to tissue, wherein said anchor comprises a second detachable element;
   wherein said first detachable element is configured to detachably engage said second detachable element to enable said anchor to remain implanted and enable said electrode to be explanted; and,
   wherein said first detachable element and said second detachable element are coupled together based on radially outward force provided by said first detachable element and radially inward force provided by said anchor,
   wherein via said radially inward force provided by said anchor, said anchor imparts force on said first detachable element.

2. The detachable electrode and anchor according to claim 1, wherein
   said first detachable element coupled with said electrode comprises at least one radially outward oriented projection; and,
   said second detachable element in said anchor comprises at least one radially outward oriented indentation configured to engage said at least one radially outward oriented projection.

3. The detachable electrode and anchor according to claim 1, wherein
   said first detachable element coupled with said electrode comprises at least one bearing; and,
   said second detachable element in said anchor comprises an indentation configured to engage said at least one bearing.

4. The detachable electrode and anchor according to claim 3, wherein said indentation comprises a ring indentation, wherein said at least one bearing engages said ring indentation via an axial rotational coupling.

5. The detachable electrode and anchor according to claim 3, wherein said indentation comprises multiple indentations that correspond with one or more of said at least one bearing, and wherein one or more of said at least one bearing engage said multiple indentations to provide a fixed rotational relationship between said leadless medical implant and said anchor.

6. The detachable electrode and anchor according to claim 1, wherein
   said first detachable element coupled with said electrode comprises a ring; and,
   said second detachable element in said anchor comprises an indentation wherein said indentation is configured to engage said ring.

7. The detachable electrode and anchor according to claim 1, wherein
   first detachable element coupled with said electrode comprises at least one radially inward oriented indentation; and,
   said second detachable element in said anchor comprises a ring configured to engage said at least one radially inward oriented indentation.

8. The detachable electrode and anchor according to claim 1, wherein
   said first detachable element comprises a temperature dependent hardness.

9. The detachable electrode and anchor according to claim 1, wherein
   said second detachable element comprises a temperature dependent hardness.

10. The detachable electrode and anchor according to claim 1, wherein
    said first detachable element and said second detachable element comprise a temperature dependent hardness.

11. The detachable electrode and anchor according to claim 1, wherein said leadless medical implant comprises a leadless pacemaker.

12. The detachable electrode and anchor according to claim 1, wherein
    said first detachable element coupled with said electrode comprises at least one radially inward oriented projection; and,
    said second detachable element in said anchor comprises at least one radially inward oriented indentation configured to engage said at least one radially inward oriented projection;
    wherein said at least one radially inward oriented projection is configured to radially retract to disengage from said at least one radially inward oriented indentation which reduces a force against said at least one radially inward oriented indentation via a longitudinal force applied to said detachable leadless medical implant and anchor.

13. The detachable electrode and anchor according to claim 1, wherein
    said first detachable element coupled with said electrode comprises at least one radially outward oriented projection; and,
    said second detachable element in said anchor comprises at least one radially outward oriented indentation configured to engage said at least one radially outward oriented projection;
    wherein said at least one radially outward oriented projection is configured to radially retract to disengage from said at least one radially outward oriented indentation which reduces a force against said at least one radially outward oriented indentation via a longitudinal force applied to said detachable leadless medical implant and anchor.

* * * * *